United States Patent
Kijlstra et al.

(10) Patent No.: US 7,338,804 B2
(45) Date of Patent: Mar. 4, 2008

(54) AUTOMATED CLINICAL ANALYZER REAGENT FORMULATION

(75) Inventors: Johan Kijlstra, Odenthal (DE); Dieter Rüehle, Odenthal-Blecher (DE); Ralf Niegl, Yorktown Heights, NY (US); Paul Gherson, Yorktown Heights, NY (US); Germaine Adriana Tarcu, Glendale, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 101 days.

(21) Appl. No.: 10/996,813

(22) Filed: Nov. 24, 2004

(65) Prior Publication Data

US 2006/0110831 A1    May 25, 2006

(51) Int. Cl.
*G01N 35/08*    (2006.01)

(52) U.S. Cl. .......................................... 436/53; 422/82

(58) Field of Classification Search ................ 436/53; 422/82
See application file for complete search history.

(56) References Cited

U.S. PATENT DOCUMENTS

| | | | | |
|---|---|---|---|---|
| 3,703,470 | A | * | 11/1972 | Brennan ..................... 510/231 |
| 4,141,687 | A | | 2/1979 | Forrest et al. |
| 5,268,147 | A | | 12/1993 | Zabetakis et al. |
| 5,399,497 | A | | 3/1995 | Kumar et al. |
| 6,485,980 | B1 | * | 11/2002 | Adolfsen et al. ............. 436/53 |
| 6,734,436 | B2 | * | 5/2004 | Faris et al. ............. 250/432 R |

OTHER PUBLICATIONS

Lyklema. Fundamentals of Interface and Colloid Science, vol. 3, pp. 1.45-1.48. Academic Press 2000.

\* cited by examiner

*Primary Examiner*—Jill Warden
*Assistant Examiner*—Natalia Levkovich
(74) *Attorney, Agent, or Firm*—Chien Yuan (57) ABSTRACT

This invention significantly reduces the frequency of hydraulic failure in the analytical line of a capsule chemistry sample liquid analysis system which can occur when the reagents required for the specific analytical test have an imperfect merger with the sample aliquot reagent in the vanish zone of the analytical line. It has been found that the dynamic surface tension of the sample aliquot reagent and the analytical reagent influence the merging process. It has also been found that optimum merging of these reagent capsules in the vanish zone can be obtained when the dynamic surface tension of the sample aliquot reagent and analytical reagent is different.

8 Claims, 6 Drawing Sheets

AUTOMATED CLINICAL ANALYZER REAGENT FORMULATION

BACKGROUND OF THE INVENTION

This invention relates to the hydraulic oil-based technology of a capsule chemistry sample liquid analysis system for the automated clinical analysis of samples of human biological fluids.

Capsule chemistry technology utilizes an oil-based segmented-flow technique combined with a noninvasive method to combine and mix each sample aliquot with the required reagents for the specific analytical test or method. This non-invasive technology is achieved by sophisticated microhydraulics, and requires no intrusion into the reaction pathway and no moving parts.

The entire analytical process, from sampling to readout, occurs in a single capillary tube referred to as the analytical line or conduit. A typical automated capsule chemistry liquid analysis system is described in U.S. Pat. No. 5,268,147 to Zabetakis et al, the disclosure of which is incorporated by reference herein.

An important part of the analytical line is an enlarged cross-sectional area known as the "vanish zone" which operates in the manner of an expanding flotation zone to combine liquid segments positioned on each side of an air segment.

Important developments in capsule chemistry technology include refinements of the geometrical dimensions of the analytical line and vanish zone; the volumes of reagent capsules; the reaction chemistry; and the physical-chemical properties of reagents, buffer, oil, probe and analytical line. Despite these refinements, hydraulic failures in the analytical line occur. These hydraulic failures can lead to anomalous analytical results due to carry-over or cross-contamination and are detected by the automated clinical analyzer system. The frequency of these hydraulic failures varies, depending on the system parameters. Hydraulic failures require in many cases the repetition of the analysis and therefore reduce the cost-effectiveness of the automated clinical analytical system.

DESCRIPTION OF THE PREFERRED EMBODIMENTS

The present invention improves the performance of automated clinical analyzers employing a vanish zone, and reduces the frequency of hydraulic failures in the analytical line of an automated clinical analysis system.

Figure 1:
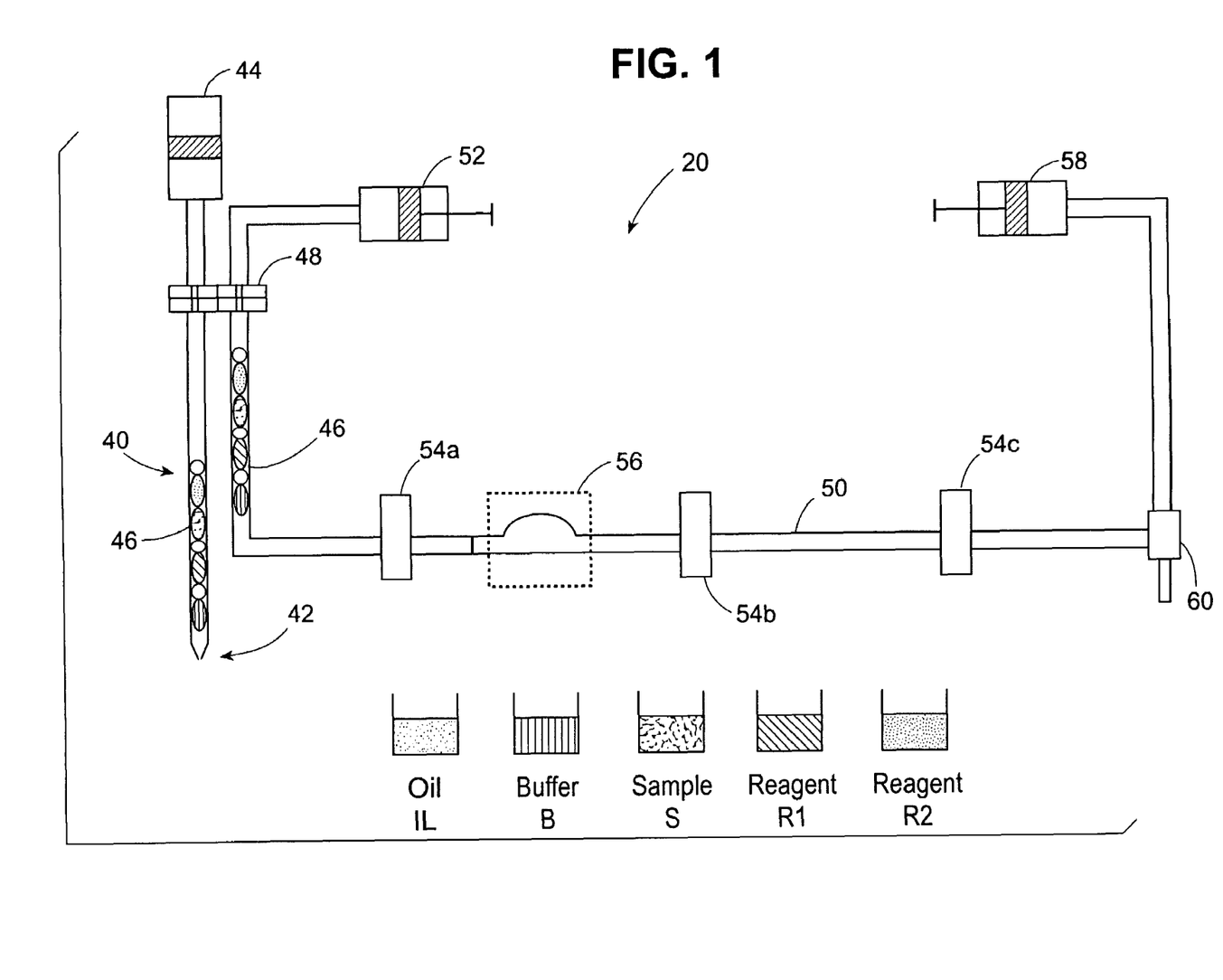
FIG. 1 is a simplified schematic representation of the principal features of an automated capsule chemistry sample liquid analysis system.
Figure 2:
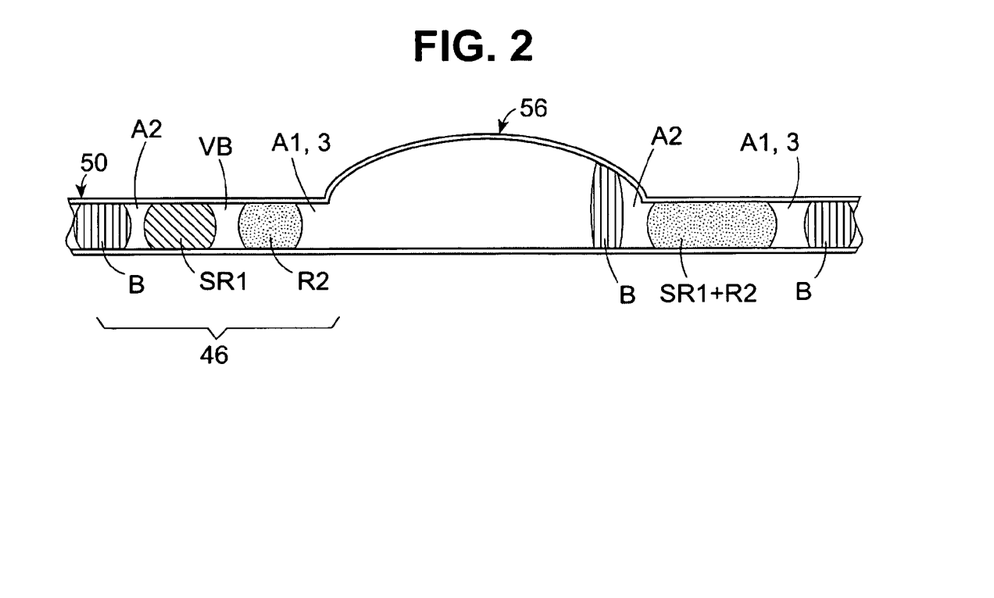
FIG. 2 is an enlarged schematic representation of a portion of the analytical line showing a test package before and after passing through the vanish zone.

The automated clinical analysis system contains a long, narrow, optically clear capillary tube preferably made of Teflon® (DuPont Co.) or like material with pumps at the near and far end. Referring to FIGS. 1 and 2, the automated clinical analysis system 20 comprises a sample liquid test package aspirating assembly 40 with a probe 42 and a pump 44 that is used to aspirate the liquid portion or aliquots of the test segments comprising the test package 46. These liquid portions include the sample S, the aqueous reagent aliquots R1 and R2, the buffer B, and the oil isolation liquid, IL, which are shown more clearly in FIG. 2.

A shear valve 48 serves to transfer the test package 46 to the analytical line 50 where pump 52 transfers the test package 46 through flow cell 54a. Flow cell 54a is used to read the optical absorbance of liquid reagents R1 and R2 before reagents R1 and R2 merge in vanish zone 56.

FIG. 2 shows an enlarged portion of the analytical line 50 with the vanish zone 56 of FIG. 1. Sample S and reagent R1 merge immediately inside the probe 42 upon aspiration to produce the reagent/sample capsule SR1. The aliquots SR1 and R2 are separated by an air segment VB, referred to as the vanish bubble. An aqueous buffer segment B, interposed between the two air segments, A2 and A1,3 respectively, is used to separate different test packages inside the analytical line 50.

After each aspiration of one test package 46, one previously aspirated test package 46 is transferred past the shear valve 48 and introduced into the analytical line 50. A "push-pull" pumping mechanism is initiated which transports the test package 46 in the analytical line 50 in a back and forth motion. This back and forth motion allows each test segment in the test package 46 several opportunities for its optical properties to be read by the flow cells 54b and 54c. Flow cells 54b and 54c read the optical absorbance of test sample/first reagent SR1, and second reagent R2 at different times after merging and passing through vanish zone 56. After each cycle, which consists of one aspiration of a test package and one back and forth motion, the next test package will be introduced into the analytical line 50. After the analysis has been completed, pump 58 disposes unwanted test package materials to waste collection 60.

The configuration and structure of the reaction capsules SR1 and R2 is influenced by the isolation liquid, IL, which wets and coats the hydrophobic inner surface of the analytical line 50 with a thin, flowing film of the isolation liquid IL. The isolation liquid is replenished continuously as new samples are aspirated into the analytical line 50.

The isolation liquid IL that coats the inner walls of the analytical line 50 is typically a fluorocarbon or silicon liquid, such as FC43™ (3M Co.), FC70™ (3M Co.), and DC 200™ (Sigma-Aldrich Co.). The isolation liquid substantially completely prevents contact with the inner surface of the analytical line 50 and is immiscible with the sample, reagent and buffer liquids, and substantially and completely excludes any residual presence or carryover of the sample, reagent, and buffer liquids on the inner surface of the analytical line 50.

In this manner, the cross-contamination of succeeding sample liquid or reagent by the residue of a preceding sample liquid or reagent is virtually eliminated, thus significantly increasing the overall accuracy of the results of the sample liquid analysis.

The technique of sample liquid carryover minimization through use of an immiscible isolation liquid in an automated sample liquids analysis system is described in the aforementioned U.S. Pat. No. 5,268,147 to Zabetakis et al, the disclosure of which is incorporated by reference herein.

The reaction is initiated by merging and mixing reaction capsules SR1 and R2 inside the vanish zone 56. Typical reactions that occur between the SR1 and R2 segments are based on the generation of color from the reaction of the analyte in the sample with reagents R1 and R2. Other typical reactions are latex agglutination assays.

In these reactions, reagent R1 is an analyte-ficoll conjugate, while R2 is a colloidal suspension of latex particles coated with an analyte specific antibody. During reaction, the analyte in the sample and the analyte in the ficoll conjugate compete over a limited quantity of the antibody attached to the latex particles. Binding of the ficoll-analyte conjugate to the latex-antibody reagent results in the formation of large molecular aggregates and increases the turbidity of the mixture. The rate of aggregate formation and the resulting increased turbidity is inversely proportional to the amount of analyte in the sample.

Other reactions can involve the analysis of human body fluids, such as blood serum, plasma, urine or cerebro-spinal fluid.

In front of the vanish zone 56, the small vanish bubble VB made of air is located between the two reaction capsules SR1 and R2 of the test package 46. Thus, vanish bubble VB provides an occluding barrier between the reaction capsules SR1 and R2 to prevent contact before they reach the vanish zone 56. However, at the vanish zone 56, the tube diameter of analytical line 50 increases significantly.

As the test package 46 enters the vanish zone 56, the small vanish bubble VB is no longer able to occlude the analytical line 50 and function as a barrier to prevent contact between reaction capsules SR1 and R2. The vanish bubble VB floats to the top of the vanish zone 56 and then appears to "vanish" as it merges with the air segment A2. When the reaction capsule SR1 of test package 46 enters the vanish zone 56, it passes beneath the vanish bubble VB and contacts and mixes with the reaction capsule R2 from the same test package 46. The desired result is a single larger combined capsule SR1 and R2 for test package 46. The contacting and mixing of the capsules SR1 and R2 initiates the reaction.

One embodiment of the invention is a method that significantly reduces the frequency of hydraulic failure in the analytical line due to imperfect merger of reagent capsules SR1 and R2 in the vanish zone. It has been found that the dynamic surface tension of both reagents R1 and R2 influence the merging process. More surprisingly, it has been found that optimum merging of the reagent capsules SR1 and R2 in the vanish zone can be obtained when the dynamic surface tension of reagent R1 and reagent R2 is different.

According to current knowledge, maximum system performance of the capsule chemistry system of the automated clinical analyzer is achieved when both test reagents R1 and R2 have equal static surface tension $\gamma_\infty$.

The surface, tension $\gamma$, is the energy that must be supplied to increase the surface area by one unit, for example, one square meter. The surface tension may be time dependent if during the expansion the surface is not at equilibrium. This is the case for solutions containing surface active additives, wherein the surface tension is referred to as dynamic surface tension $\gamma_d$.

Figure 3:
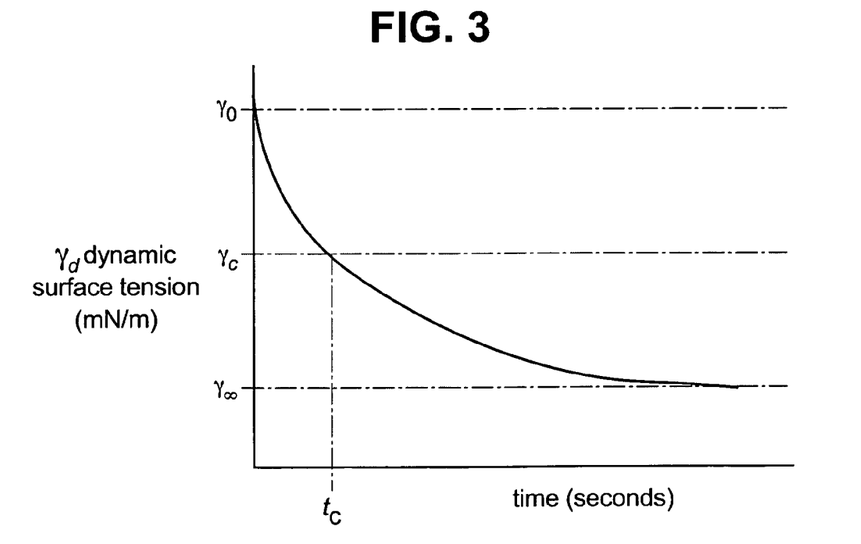
FIG. 3 is a graph showing the time decay of the dynamic surface tension $\gamma_d$ of an aqueous solution containing surface active compounds.

FIG. 3 is a graph showing the time decay of the dynamic surface tension $\gamma_d$ of an aqueous surfactant solution. At extended periods of time, the dynamic surface tension yd equals the equilibrium static surface tension $\gamma_\infty$. At very short time intervals the surfactant does not influence the surface tension, which attains the surface tension value $\gamma_0$ of pure water.

The static surface tension $\gamma_\infty$ of aqueous solutions can be measured by using the standard Du Noüy ring technique. See J. Lyklema, *Fundamentals of Interface and Colloid Science*, Volume III, p. 1.45-1.48 (Academic Press, 2000). The dynamic surface tension $\gamma_d$ of aqueous solutions can be measured by using suitable commercially available equipment and methods such as the bubble pressure tensiometer MPT2™ (Lauda GMBH & Co. KG).

Figure 4:
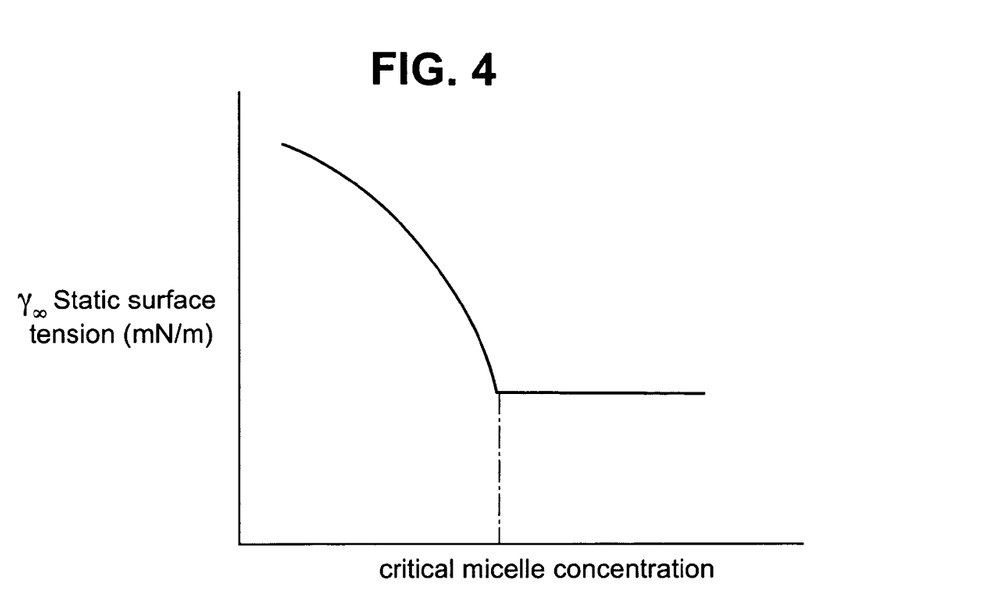
FIG. 4 is a graph showing the determination of critical micelle concentration from measurements of static surface tension as a function of surfactant concentration.

Surfactant solutions have a critical micelle concentration cmc, that represents the bulk concentration above which micelles, or small aggregates of associated surfactant molecules form. The critical micelle concentration can be determined by measuring the static surface tension as a function of the surfactant concentration C, as shown graphically in FIG. 4.

Above the critical micelle concentration most added surfactant is micellized and does not affect the equilibrium static surface tension $\gamma_\infty$. This means that above the critical micelle concentration the equilibrium static surface tension $\gamma_\infty$ is independent of the surfactant concentration. This does not generally hold true for the dynamic surface tension $\gamma_d$, which above the critical micelle concentration also varies with changing surfactant concentration.

In practice, the surfactant concentration C is always greater than the critical micelle concentration. Performance changes are observed as surfactant concentration varies above the critical micelle concentration. The surfactant concentration can be varied by keeping the static surface tension constant. At the same time a change in merging performance in the vanish zone is observed. Hence, the static surface tension is not the primary parameter that determines the merging performance.

According to the present invention, the dynamic surface tension of the reagents is adjusted, and this change is accomplished by changing the surfactant concentration, even above the critical micelle concentration.

The static surface tension of test reagents R1 and R2 can range from about 15 milliNewtons/meter (mN/m) to about 60 mN/m at about 20° C. to about 50° C., preferably about 25 nN/m to about 50 mN/m at about 30° C. to about 40° C., and most preferably about 30-35 nN/m at about 37° C.

It has been found that the desired static surface tension $\gamma_\infty$ can be obtained by contacting suitable surface active molecules, such as surfactants or surfactant mixtures and water soluble polymers with each test reagent. Surfactants such as non-ionic compounds, anionic compounds, cationic compounds, amphoteric compounds, and water soluble polymers can be used.

Examples of nonionic surfactants include ethoxylated alcohols, ethoxylated alkylphenols, ethoxylated acids, fatty acid alkanolamides, ethoxylated alkanolamides, ethoxylated amines, esters of polyhydroxy compounds, ethoxylated esters, ethylene oxide/propylene oxide block copolymers and amine oxides.

Examples of anionic surfactants include alkylbenzenesulfonates, alkyl sulfates, alkyl ether sulfates, α-olefinsulfonates, alkanesulfonates, Examples of cationic and amphoteric surfactants include fatty quaternary ammonium salts, benzylalkyldimethylammonium salts, amino acids, carboxybetaines and lecithin.

Examples of water soluble polymers include synthetic polymers and biopolymers. Examples of water-soluble synthetic polymers include polyethylene oxide, polyacrylic acid, polyacrylamide, polymethacrylic acid, polystyrenesulfonic acid, polymethacrylamide, polyvinylpyrrolidone, polyvinyloxazolidone, polyvinylmethyloxazolidone, polyvinyl alcohol, polyvinyl acetate and their block copolymers.

Examples of biopolymers include cellulose ethers, gelatin, natural gums, starch and their derivatives. About 0.05 weight % to about 5.0 weight % of surfactants and/or water soluble polymers and preferably about 0.1 to about 2.5 weight % are added to each test reagent. Different amounts and different surface tension additives can be used with each test reagent. Test reagents can be prepared by mixing aqueous solutions of reagents and surface tension additives.

The test reagents for the analysis are generally aspirated from reagent bottles by an automated clinical analyzer.

The flow characteristics of the reagent capsules SR1 and R2 as they move through the analytical line can be determined by the flow times $t_{R2}$ and $t_{SR1}$, as follows:

$$t_{SR1} = \frac{l_{Sr1}}{v},$$

$$t_{R2} = \frac{l_{R2}}{v}$$

wherein $l_{SR1}$ is the length of reagent capsule SR1;
$l_{R2}$ is the length of reagent capsule R2; and
v is the characteristic translation velocity that both reagent capsules SR1 and R2 move in the forward direction through the analytical line 50 before they enter the vanish zone 56. Therefore, v is identical for both reagent capsules SR1 and R2.

A typical example of the time decay of dynamic surface tension $\gamma_d(t)$ of an aqueous solution containing surface active compounds is shown in FIG. 3, wherein $\gamma_0$ equals the dynamic surface tension extrapolated towards zero time. For aqueous solutions $\gamma_0$ is the value of pure water. $\gamma_\infty$ equals the dynamic surface tension extrapolated towards infinite time, that is, the static surface tension.

$\gamma_c$ is the characteristic dynamic surface tension, defined by the equation:

$$\gamma_c = \gamma_\infty + \frac{\gamma_0 - \gamma_\infty}{2},$$

wherein $t_C$ is the relaxation time at which $\gamma_d = \gamma_c$

The dynamic surface tension behavior is indicated by the dimensionless relaxation time $\tau_c(i)$, which is defined by the equation:

$$\tau_c(i) = \frac{t_c}{t_i},$$

wherein
$t_C$=the relaxation time wherein $\gamma_d = \gamma_c$
$t_i$=flow time, wherein i denotes the type of reagent capsule, R1, SR1 or R2.

High-speed video analysis has shown that a major class of hydraulic failures in the analytical line were due to imperfect merging of the reagents inside the vanish zone. Consequently, anomalous analytical results can occur.

To obtain such information, a video camera with a field of view comparable with the size of the vanish zone, on the order of about 15×10 mm, and a frame rate of about 500 frames per second can be used. The field of view is illuminated to clearly show the air-liquid interfaces defining the SR1 and R2 segments flowing through the vanish zone. The flow of many segments is recorded on magnetic tape, then played back at a much slower frame rate in order to determine the typical behavior of the air-liquid interfaces.

During such analysis, the speed of progression of interfaces and their shape is determined. Whenever anomalous behavior of such interfaces is detected, an effort is made to determine what physical conditions, such as vanish zone geometry, and/or reagent properties led to the anomaly.

An example of an optimal merger is the immediate and complete merger when contact occurs between capsules SR1 and R2. This usually occurs within the first one-third part of the vanish zone. An imperfect merger is when immediate and complete merger does not occur upon contact between capsules SR1 and R2. The occurrence of an imperfect merger is believed to be due to the development of a phase boundary between SR1 and R2 which prevents or delays the merging and mixing process. In contrast, with an optimal merger, any phase boundary between SR1 and R2 should disappear within the first one-third part of the vanish zone.

It has been found that the dynamic surface tension of each reagent R1 and R2 needs to be different to optimize the merging process of the reagent capsules SR1 and R2 in the vanish zone.

The type and amount of surface active compounds of the reagent R2 are chosen such that the dimensionless relaxation time $\tau_C(R2)$ ranges from about 0.04 to about 4, preferably from about 0.1 to about 3, and more preferably from about 0.2 to about 2 at the application temperature.

The type and amount of surface active compounds of the reagent R1 are chosen such that the dimensionless relaxation times $\tau_C(R1)$ and $\tau_C(R2)$ are different, in accordance with the following relationship, wherein:

$$\frac{\tau_c(R1)}{\tau_c(R2)}$$

is a positive value up to about less than about 0.5 or greater than about 2, preferably, up to about less than about 0.25 or greater than about 5, and more preferably, up to about less than about 0.1 or greater than about 12, wherein $\tau_c$ values are specified at the application temperature.

The type and amount of surface active compounds of the reagent R1 are chosen such that the dimensionless relaxation times $\tau_C$ of SR1 and R2 are different, in accordance with the following relationship, wherein:

$$\frac{\tau_c(SR1)}{\tau_c(R2)}$$

is a positive value up to about less than about 0.5 or greater than about 2, preferably, up to about less than about 0.25 and greater than about 5, and more preferably up to about less than about 0.1 or greater than about 12, wherein $\tau_c$ values are specified at the temperature of application.

The application temperature can vary from about 1° C. to about 90° C., preferably about 20° C. to about 60° C., most preferably about 30° C. to about 40° C.

Experiments were carried out on the Advia IMS 800i™ Test Station. (Bayer Corp.) Test packages with predetermined static and dynamic surface tensions containing reagent capsules SR1 and R2, separated by buffer segments and air as depicted in FIG. 2 were transported through the analytical line 50 and vanish zone 56.

The analytical system operating parameters appear in Table 1. The buffer segment that separated the test packages inside the analytical line of the Advia IMS analytical system consisted of an alkaline solution of the nonionic surfactant PlurafacRA20™ (BASF Corporation), a monofunctional linear alcohol alkoxylate.

TABLE 1

Standard Advia IMS Test Station Parameters

| Analytical Line | Vanish Zone | Characteristic Flow Rate, v | Temperature | Buffer Composition |
|---|---|---|---|---|
| Teflon ® PFA Inner radius 1.15 mm Length ca. 2 m | Expanded part of the analytical line: Length 10 mm Width 2.5 mm Height 3.0 mm Inlet angle 17° | 8 cm/s | 37° C. | 2.0 g/l NaOH 1.2 g/l Plurafac RA20 (BASF Corp.) |

A series of 120 aspirated tests was run on the Advia IMS analytical system.

As already noted, optimal merger occurs when the merging process has been completed within the first one-third part of the vanish zone. The merging performance is defined as the percentage of the total number of tests wherein the SR1 and R2 capsules merged optimally.

The experimental procedure followed the sequence of FIG. 1 and U.S. Pat. No. 5,268,147 to Zabetakis et al.

Using a metering pump, a small aliquot of the isolation liquid was aspirated from an oil reservoir into the probe. The aliquot of isolation liquid is used to maintain the protective film inside the analytical line. An air segment was then aspirated into the probe.

As shown in FIG. 2, the metering pump sequentially aspirated into the probe the air segment (Air 1,3), the reagent R2, the vanish bubble VB, the sample S, the reagent R1, the air segment (Air 2) and the aqueous buffer segment.

The typical volumes of each of the aspirated segments are listed in Table 2.

TABLE 2

Aspiration Order And Test Package Segment Volumes (microliters)

| Isolation Liquid (IL) | Buffer | Air2 (A2) | Sample (S) | Reagent 1 (R1) | Vanish Bubble | Reagent 2 (R2) | Air1, 3 (A 1, 3) |
|---|---|---|---|---|---|---|---|
| 2 µl | 7 µl | 11 µl | 1.0 µl | 14.0 µl | 4.7 µl | 14.5 µl | 17 µl |

From the volume V(R2) of reagent capsule R2 (14 µl), the inner radius r of the analytical line (1.15 mm) and the characteristic translation velocity v of 80 mm/s, $$l_{R2} = \frac{V(R2)}{\pi \cdot r^2} = 3.4 \text{ mm}$$

$$t_{R2} = \frac{l_{R2}}{v} = \frac{3.4}{80} \cdot 1000 = 43 \text{ milliseconds}$$

The examples investigated the influence of the surface properties of the reagent capsules SR1 and R2 on the merging behavior inside the vanish zone. Experiments with samples and reagents with predetermined properties of dynamic and static surfactants were conducted. Experiments with "model reagents", that is reagents without biological components having different surface properties were conducted. The surfactant solutions consisted of aqueous solutions of varying concentration of the nonionic surfactant Triton® X-100 (Dow Co.), an octylphenol ethoxylate containing 9 to 10 moles of ethylene oxide.

The critical micelle concentration of Triton® X-100 is 0.12 g/l at 37° C. In the experiments, the Triton® X-100 concentration of the model reagents representing R1 and R2 was varied between 0.1 and 10.0 g/l above the critical micelle concentration.

Table 3 lists the different values for the static surface tensions $\gamma_0$, $\gamma_\infty$ and $\gamma_c$ of the Triton® X-100 solutions at concentrations above the critical micelle concentration.

TABLE 3

Values for $\gamma_0$, $\gamma_\infty$ and $\gamma_c$ of Triton ® X-100 Solutions At Concentrations Above The Critical Micelle Concentration @ 37° C.

| | |
|---|---|
| $\gamma_0$(mN/m) | 66 |
| $\gamma_\infty$(mN/m) | 32 |
| $\gamma_c$(mN/m) | 49 |

Figure 5:
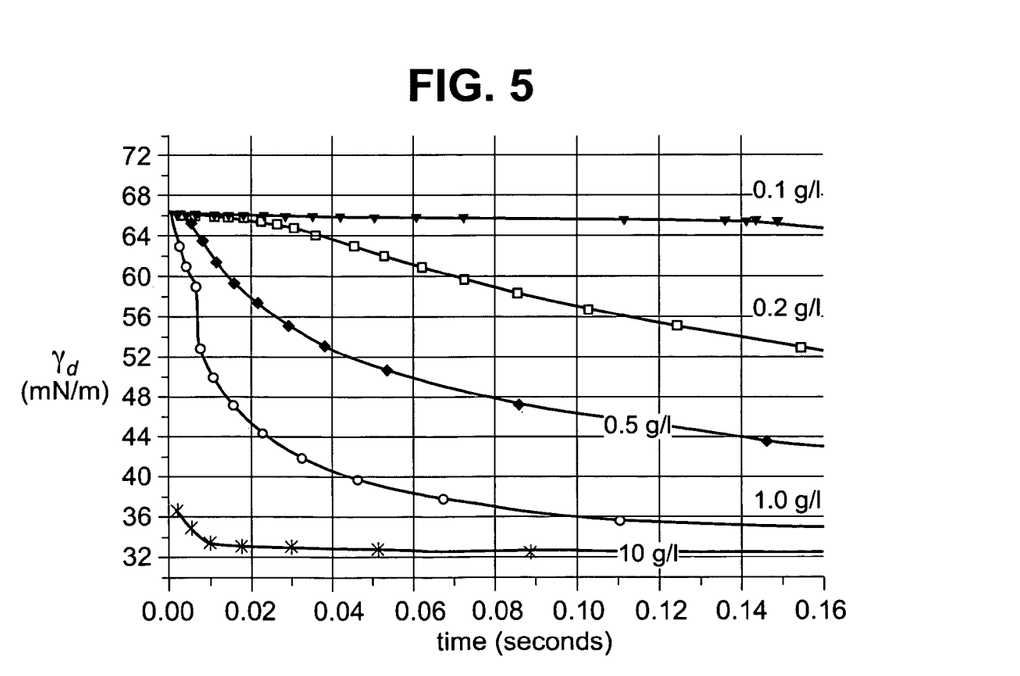
FIG. 5 is a graph showing the dynamic surface tension of various concentrations of a nonionic surfactant solution at 37° C.

FIG. 5 shows the dynamic surface tension of the Triton® X-100 solutions as a function of the surfactant concentration varying from 0.1 to 10 g/liter.

Table 3 show the dimensionless relaxation time $\tau_C$ obtained for each Triton® X-100 (Dow Co.) surfactant solution. The corresponding values for the relaxation time $t_c$ are also shown in Table 4.

TABLE 4

Relaxation Times $t_c$ and Dimensionless Relaxation Times $\tau_c(i)$ as Function of Triton ® X-100 Concentration

| Triton ® X-100 concentration (g/l) | $t_c$(23° C.) (milliseconds) | $\tau_c$ (23° C.) | $t_c$(37° C.) (milliseconds) | $\tau_c$ (37° C.) |
|---|---|---|---|---|
| 0.1 | >150 | >3.5 | >150 | >3.5 |
| 0.2 | >150 | >3.5 | >150 | >3.5 |
| 0.5 | 39 | 0.92 | 71 | 1.45 |
| 1.0 | 15 | 0.35 | 13 | 0.27 |
| 10 | 1 | 0.02 | <1 | <0.02 |

To calculate $\tau_c(i)$ from $t_c$, the characteristic flow time $t_{R2}$ of 43 milliseconds (ms) was used. This is the standard value of the Advia IMS Test Station.

In the examples which follow, all parts and percentages are by weight, unless otherwise noted.

EXAMPLE 1

Double test runs with water solutions of Triton® X-100 as model reagents were carried out on the Advia IMS™ Automated Clinical Analyzer (Bayer Corp.). A double test run means that during one experimental run, only two types of test packages were aspirated alternately in series for at least 120 times.

In this example, aqueous Triton® X-100 surfactant solutions without biological components were used as model reagents R1 and R2. Different concentrations of Triton® X-100 solutions were used, but the concentration was always the same for both model reagents R1 and R2 of any test package. Consequently, the static and dynamic surface tension values for both model reagents R1 and R2 of any test were identical. The identical surfactant concentration in R1 and R2 results in identical dynamic surface tension for both reagents. Three different test packages were investigated wherein the Triton® X-100 concentration in R1 and R2 was 0.1, 1.0 and 10 g/l. For all test packages, the same surfactant solution, Triton® X100, was chosen for sample S and reagent R1. Hence, the surface properties, that is static and dynamic surface tension of capsule SR1 were the same as that of reagent R1.

Figure 6:
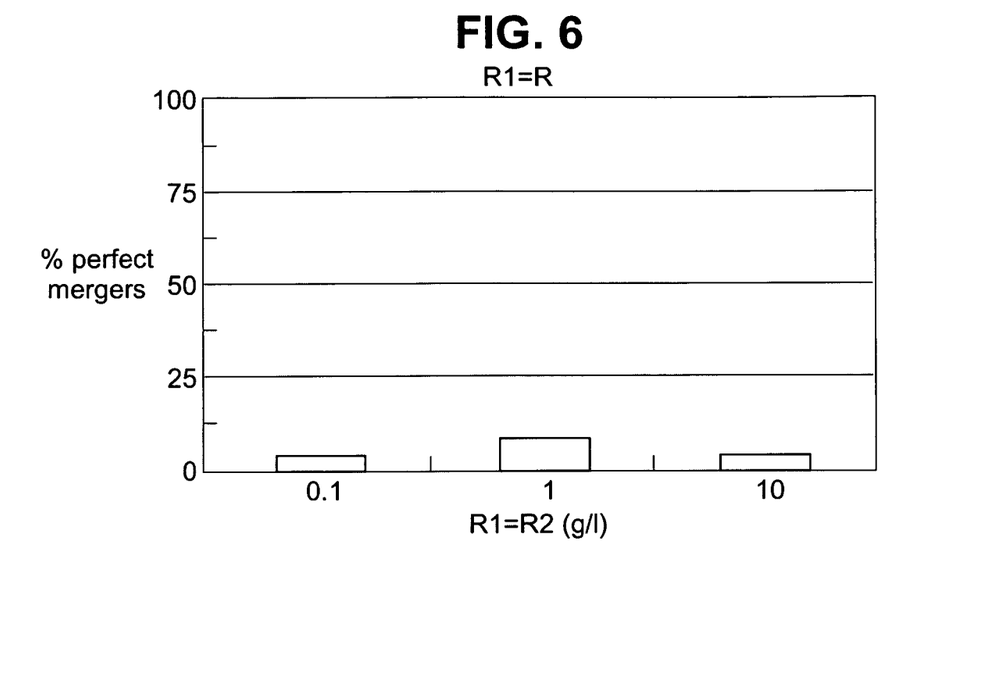
FIG. 6 is a graph showing the merging performance of identical reagents inside the vanish zone.

As a reference test package, the test package with the Triton® X-100 concentration of 1 g/l was used. During a double test run, this reference test package was aspirated always in combination with a second model test package of either 0.1 g/l or 1.0 g/l or 10 g/l. The static surface tension of all model reagents was approximately 32 mN/m at 37° C. The corresponding values for the dynamic surface tension are displayed in FIG. 5. FIG. 6 depicts the merging results according to high speed video analysis.

This example shows that the merging performance, that is, the percentage of optimal merges is less than 10%, and therefore unsatisfactory. From this example, it can be concluded that when each reagent R1 and R2 have the identical surfactant concentrations, there generally results an imperfect merger of SR1 and R2 in the vanish zone of the analytical line. This is because the identical surfactant concentration results in the same dynamic surface tension for each reagent R1 and R2 and this does not give good performance.

EXAMPLE 2

Single test runs with Triton® X-100 solutions as model reagents were carried out on the Advia IMS Clinical Analyzer. A single test run means that during one experimental run, only one type of test package was aspirated in series for at least 120 times. In this example, the Triton® X-100 concentration in both model reagents R1 and R2 for each test package was different. Four types of test packages were investigated. They were characterized by different Triton® X-100 concentration in both reagents R1 and R2, that is, R1/R2: 10/1, 10/0.5, 1.0/1.0 and 1.0/10, in grams/liter (g/l).

Figure 7:
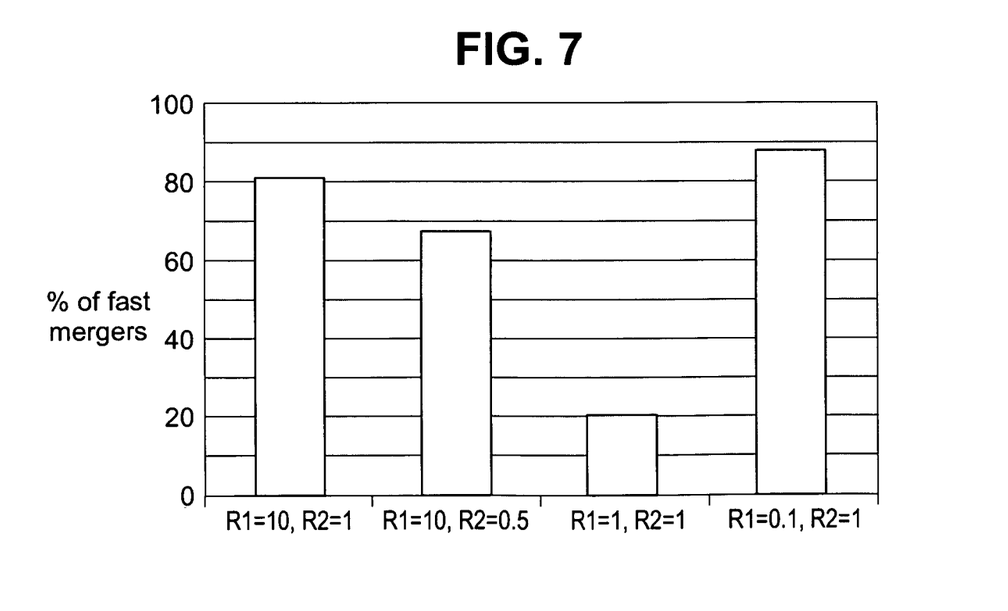
FIG. 7 is a graph showing the merging performance of different reagents inside the vanish zone.

For all test packages, the same surfactant solution was chosen for sample S and reagent R1. Hence, the surface properties of capsule SR1 was the same as that of reagent R1. The static surface tensions of all model reagents was approximately equal, about 32 mN/m at 37° C. In contrast, the dynamic surface tensions of these model reagents vary as a function of their Triton® X-100 concentration. See FIG. 5. The corresponding values for $$\frac{\tau_c(SR1)}{\tau_c(R2)}$$

appear in Table 5. FIG. 7 depicts the merging results according to high speed video analysis.

TABLE 5

$\dfrac{\tau_c(SR1)}{\tau_c(R2)}$ Values For The Test Packages Investigated

| | Triton ® X-100 concentration in SR1 | Triton ® X-100 concentration in R2 | $\tau_c(SR1)$ | $\tau_c(R2)$ | $\dfrac{\tau_c(SR1)}{\tau_c(R2)}$ |
|---|---|---|---|---|---|
| (a) | 10 | 1.0 | <0.02 | 0.27 | <0.07 |
| (b) | 10 | 0.5 | <0.02 | 1.45 | <0.01 |
| (c) | 1.0 | 1.0 | 0.27 | 0.27 | 1.0 |
| (d) | 0.1 | 1.0 | >3.5 | 0.27 | >13.0 |

This example demonstrates that the merging performance can be significantly improved when the respective surfactant concentrations in reagents R1 and R2 are different. This difference in surfactant concentration causes an imbalance in the dynamic surface properties of the reagent capsules, which is believed to improve the merging behavior in the vanish zone. The difference in the dynamic surface properties of reagents R1 and R2 is characterized by the ratio of dimensionless relaxation times $$\frac{\tau_c(SR1)}{\tau_c(R2)},$$

which is a function of the surfactant concentrations in both reagents R1 and R2. From these results it can be concluded that:

1. Even at surfactant concentrations above the critical micelle concentration, where the static surface tension is independent of the surfactant concentration, the dynamic surface tension behavior of the surfactant solutions strongly depends on the surfactant concentration;
2. Adjustment of the static surface tension of both reagents R1 and R2 by adjusting the surfactant concentration, which is not the same for each reagent, is insufficient to optimize the merging process inside the vanish zone;
3. Adjustment of the surfactant concentration of R1 and R2 so that the dynamic surface tension of each reagent is different, results in a significant improvement of the merging process;
4. Adjustment of $$\frac{\tau_c(SR1)}{\tau_c(R2)}$$

to a positive value up to less than about 0.5 or greater than about 2 results in a significant improvement of the merging process.

EXAMPLE 3

Double test runs with Triton® X-100 solutions as model reagents were carried out on the Advia IMS, similar to the procedures in Examples 1 and 2. During each run, two types of tests, ai and bi were conducted, wherein i ranges from 1-5. Test packages "a" and "b" were aspirated alternately in series. For all tests, the same surfactant solution, Triton® X-100, was chosen for sample S and reagent R1. Hence, the surface properties of capsule SR1 was the same as that of reagent R1.

Different surfactant concentrations were chosen for R1 and R2 for all test packages except a4 and b4. The test results are given in Table 6.

Figure 8A:
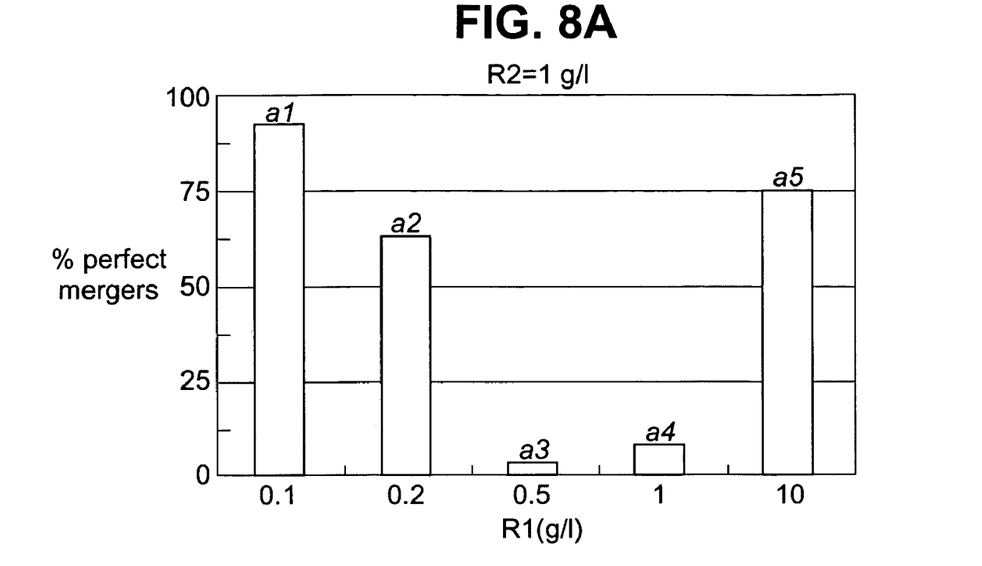
FIGS. 8a and 8b are graphs showing the merging performance of model reagents R1 and R2, respectively.
Figure 8B:
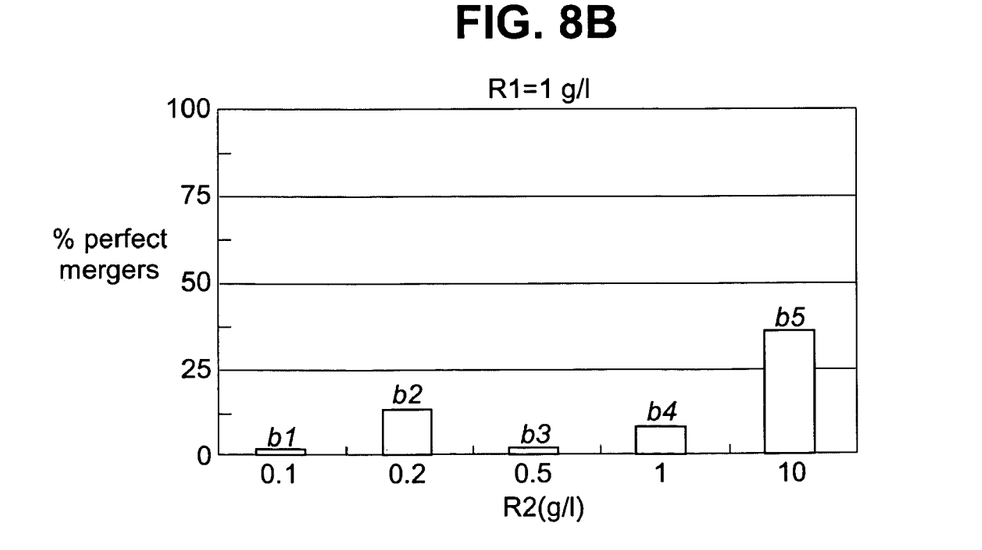

The static surface tension of all model reagents was equal to about 32 mN/m at 37° C. FIGS. 8a and 8b show the merging results according to high speed video analysis. These merging results can be correlated to the degree of imbalance in the dynamic surface properties of both reagents R1 and R2, as characterized by the value of $$\frac{\tau_c(SR1)}{\tau_c(R2)}$$

in Table 6. By combining the data in Table 6 with the results in FIGS. 8a and 8b, it can be concluded that:

1. Very poor merging performance was obtained for all test packages b1-b5, that is, when the Triton®X-100 concentration in SR1 equaled 1 g/l, corresponding to a $\tau_c(SR1)$ value of 0.27. By varying the Triton®X-100 concentration of R2, and keeping the concentration of R1 constant, the values $\tau_C(R2)$ and $$\frac{\tau_c(SR1)}{\tau_c(R2)},$$

the merging performance was not satisfactorily improved. The percent of optimal mergers were less than 50%.

2. The merging performance test packages a1-a5, that is, when the Triton®X-100 concentration of R2 was kept constant at 1 g/l, corresponding to a $\tau_C(SR2)$ value of 0.27, varies as a function of the Triton®X-100 concentration of R2. Hence, at both low and high Triton®X-100 concentrations of SR1, that is, those <0.5 and >1.0 g/l, which correspond to $\tau_C(SR1)$ values of >3.5 and <0.27, respectively, good merging performance was obtained. The amount of optimal mergers was greater than 50%.

3. At intermediate Triton®X-100 concentrations of SR1, that is, 0.5 and 1.0 g/l, corresponding to $\tau_C(SR1)$ values of 1.45 and 0.27, respectively, poor merging performance occurred. The percent perfect mergers was less than 50%.

From this it can be concluded that the merging performance depends both on the absolute value of $\tau_C(R2)$ which preferably should have an intermediate value on the order of about 0.04 to about 4.0, and on the ratio

TABLE 6

Test Packages And $\frac{\tau_c(SR1)}{\tau_c(R2)}$ Values.

| Test package | Triton ® X-100 concentration in SR1 | Triton ® X-100 concentration in R2 | $\tau_c(SR1)$ | $\tau_c(R2)$ | $\frac{\tau_c(SR1)}{\tau_c(R2)}$ |
|---|---|---|---|---|---|
| a1 | 0.1 | 1.0 | >3.5 | 0.27 | >13 |
| a2 | 0.2 | 1.0 | >3.5 | 0.27 | >13 |
| a3 | 0.5 | 1.0 | 1.45 | 0.27 | 5.4 |
| a4 | 1.0 | 1.0 | 0.27 | 0.27 | 1.0 |
| a5 | 10 | 1.0 | <0.02 | 0.27 | <0.07 |
| b1 | 1.0 | 0.1 | 0.27 | >3.5 | <0.08 |
| b2 | 1.0 | 0.2 | 0.27 | >3.5 | <0.08 |
| b3 | 1.0 | 0.5 | 0.27 | 1.45 | 0.19 |
| b4 | 1.0 | 1.0 | 0.27 | 0.27 | 1.0 |
| b5 | 1.0 | 10 | 0.27 | <0.02 | 14 |

$$\frac{\tau_c(SR1)}{\tau_c(R2)},$$

which preferably should have a value much smaller or much larger than 1.0, in the range of <0.5 or >2.0.

EXAMPLE 4

Data was collected from the Advia IMS System (Bayer Corp.) during the the Reagent Base Line (RBL) test. This test measures the optical absorbance of the reagents and is performed by the system automatically every 24 hours. The RBL run consists of five replicates of each reagent or method, such as Glucose (Glu) and Total Bilirubin (TBili), using a solution with negligible optical absorbance, such as saline/0.1% Triton X-100 as a sample.

The merging performance was evaluated based on the direction of vanishing inside the vanish zone. Vanishing that occurs in the forward direction in the first one-third portion of the vanish zone is considered the perfect merge. A forward vanish is defined as a vanish event that occurs on the forward direction or slosh. This is the desired vanishing event.

If the Air 1,3 (see FIG. 2) after vanish does not increase in size more than 3 uL, then the direction of vanish is marked as "forward" (F). If the volume of Air 1,3 after vanish increases more than 3 uL, then the event occurs in "backwards" (B) slosh. The type of vanish direction is identified automatically from the detection and software system of the Advia IMS System.

Figure 9:
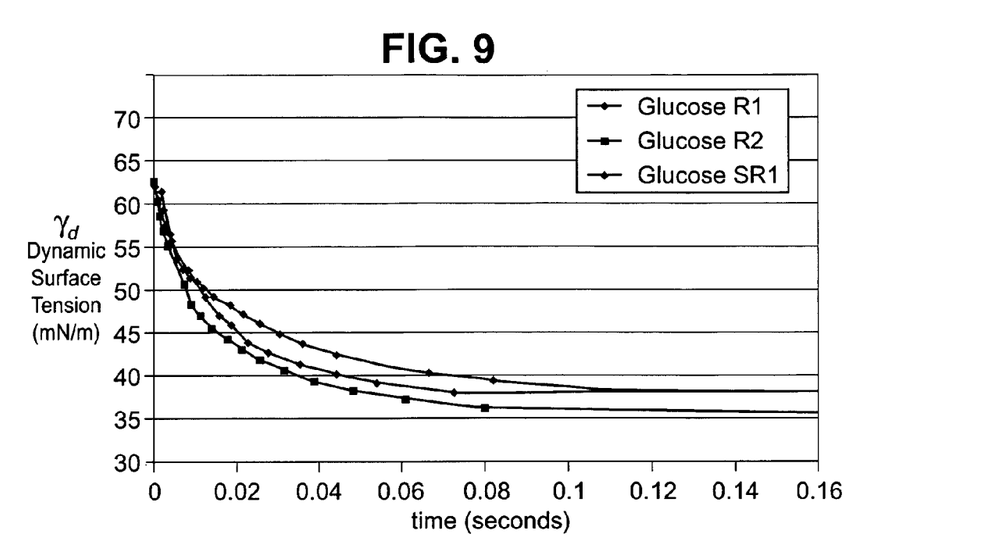
FIG. 9 is a graph showing the dynamic surface tension of glucose reagent capsules.
Figure 10:
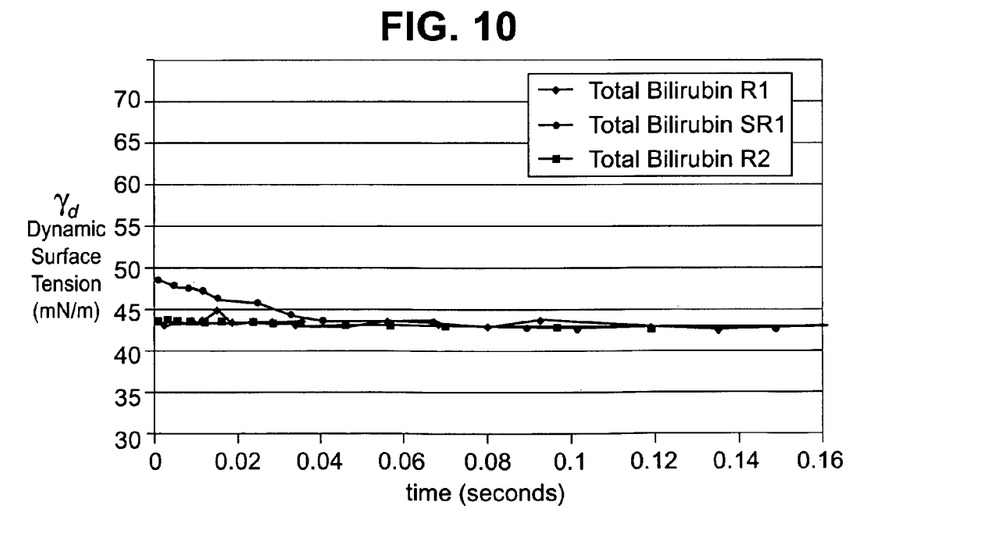
FIG. 10 is a graph showing the dynamic surface tension of bilirubin reagent capsules

The results in Table 7 show that the merging performance in the desired forward mode for the Glucose method is much better than that of the Total Bilirubin method. This can be related to the rather high static surface tension $\gamma_\infty$ and the very low dimensionless times $\tau_C$ of the Total Bilirubin reagents. See FIGS. 9 and 10 and Table 8. Data from FIGS. 9 and 10 was used to establish information on Table 8.

TABLE 8

Characteristic Parameters For Glucose and Total Bilirubin Reagents at 37° C.

| Test package | $\gamma_0$ (mN/m) | $\gamma_\infty$ (mN/m) | $\gamma_c$ (mN/m) | $t_c$ (SR1) (ms) | $t_c$ (R2) (ms) | $\tau_c$ (SR1) (−) | $\tau_c$ (R2) (−) |
|---|---|---|---|---|---|---|---|
| Glucose | 66 | 32 | 49 | 14 | 12 | 0.33 | 0.28 |
| Total Bilirubin | 66 | 43 | 55 | <1.0 | <1.0 | <0.02 | <0.02 |

To calculate $\tau_c(i)$ from $t_c$, a value of 43 ms for the characteristic flow time $t_{SR1}=t_{R2}$ was used.

Although this invention has been described in the context of improving the merger of a test sample/first reagent, SR1, with a second reagent, R2, in the vanish zone of the analytical line of an automated clinical analyzer, it can have broader application to other types of reactions wherein the successful merging of a first reagent and a second reagent is important, such as in the synthesis of various chemical compositions, and wherein the success of such a merger is dependent on the difference in dynamic surface tension of the first reagent from the dynamic surface tension of the second reagent.

What is claimed is:

1. A method for improving the merging of a test sample/first reagent, SR1, with a second reagent, R2, to form merged SR1+R2 in a vanish zone of a capillary analytical line in an automated clinical analyzer utilizing a hydraulic capsule chemistry sample liquid analysis system for the analysis of human biological fluids, comprising:
    a) hydraulically introducing into the analytical line a test package comprising liquid segments of a test sample S, a first reagent R1 and a second reagent R2;
    b) contacting each reagent segment R1 and R2 with a suitable surface active compound to adjust the dynamic surface tension of each reagent segment R1 and R2, so

TABLE 7

Merging performance of Glucose and Total Bilirubin on the Advia IMS Forward (F) and Backward (B) Vanish Direction

| Sample Name | Method Name | Air 1, 3 Before Vanish (BV) | Air 1, 3 After Vanish (AV) | Air 1, 3 AV-Air 1, 3 BV | Vanish Direction |
|---|---|---|---|---|---|
| RBL solution bulk (Saline/Triton X-100) | GLU | 21.0 | 21.0 | 0.0 | F |
| | GLU | 21.0 | 21.0 | 0.0 | F |
| | GLU | 21.0 | 22.4 | 1.4 | F |
| | GLU | 21.0 | 21.0 | 0.0 | F |
| | GLU | 19.6 | 19.6 | 0.0 | F |
| | GLU | 20.6 | 19.3 | −1.4 | F |
| | GLU | 19.3 | 20.6 | 1.4 | F |
| | GLU | 20.6 | 20.6 | 0.0 | F |
| | GLU | 19.3 | 20.6 | 1.4 | F |
| | GLU | 19.3 | 20.6 | 1.4 | F |
| RBL solution bulk (Saline/Triton X-100) | T. BIL | 25.2 | 32.2 | 7.0 | B |
| | T. BIL | 21.0 | 26.6 | 5.6 | B |
| | T. BIL | 22.4 | 28.0 | 5.6 | B |
| | T. BIL | 21.0 | 26.6 | 5.6 | B |
| | T. BIL | 21.0 | 28.0 | 7.0 | B |
| | T. BIL | 21.0 | 26.6 | 5.6 | B |
| | T. BIL | 21.0 | 28.0 | 7.0 | B |
| | T. BIL | 21.0 | 26.6 | 5.6 | B |
| | T. BIL | 21.0 | 26.6 | 5.6 | B |
| | T. BIL | 21.0 | 26.6 | 5.6 | B | that the dynamic surface tension of R1 is different from the dynamic surface tension of R2;

c) contacting the test sample S and the reagent R1 in the analytical line to form mixed reagent/sample SR1; and d) hydraulically transporting the mixed test sample/first reagent SR1 and the second reagent R2 into the vanish zone of the analytical line, to form merged SR1+R2.

2. The method of claim 1, wherein the dynamic surface tension behavior of the second reagent, R2, is indicated by the dimensionless relaxation time, $\tau_C(R2)$, and wherein the dynamic surface tension behavior of the test sample/first reagent SR1 is indicated by the dimensionless relaxation time, $\tau_C(SR1)$, and wherein $$\frac{\tau_c(SR1)}{\tau_c(R2)}$$

is a positive value up to about less than 0.5 or greater than about 2.

3. The method of claim 1, wherein complete merger between SR1 and R2 occurs within the first one-third part of the vanish zone.

4. The method of claim 1, wherein the dynamic surface tension behavior of first reagent, R1 is indicated by the dimensionless relaxation time, $\tau_C(R1)$, and the dynamic surface tension behavior for the second reagent, R2, is indicated by the dimensionless relaxation time, $\tau_C(R2)$, and wherein $$\frac{\tau_c(R1)}{\tau_c(R2)}$$

is a positive value up to about less than 0.5 or greater than about 2.

5. The method of claim 4, wherein the dimensionless relaxation time $\tau_C(R2)$ varies from about 0.04 to about 4.

6. The method of claim 1, wherein the adjustment of the dynamic surface tension is accomplished by adding surface active compounds to reagents R1 and R2 such that the static surface tension of each reagent R1 and R2 is less than about 50 in N/m.

7. The method of claim 6, wherein the surface active compounds are surfactants selected from the group consisting of nonionic compounds, anionic compounds, cationic compounds, amphoteric compounds, water soluble polymers, and mixtures thereof.

8. The method of claim 6, wherein when the surface active compounds include a nonionic surfactant, the nonionic surfactant is a monofunctional linear alcohol alkoxylate.

* * * * *